United States Patent
Yamazaki et al.

(10) Patent No.: US 8,511,142 B2
(45) Date of Patent: Aug. 20, 2013

(54) SUBSTANCE DETECTION SENSOR

(75) Inventors: Hiroshi Yamazaki, Osaka (JP); Toshiki Naito, Osaka (JP); Hiroyuki Hanazono, Osaka (JP)

(73) Assignee: Nitto Denko Corporation, Osaka (JP)

( * ) Notice: Subject to any disclaimer, the term of this patent is extended or adjusted under 35 U.S.C. 154(b) by 285 days.

(21) Appl. No.: 12/654,483

(22) Filed: Dec. 22, 2009

(65) Prior Publication Data
US 2010/0176827 A1    Jul. 15, 2010

(30) Foreign Application Priority Data

Jan. 13, 2009 (JP) .................. 2009-005091

(51) Int. Cl.
*G01N 7/00* (2006.01)
*G01R 27/08* (2006.01)

(52) U.S. Cl.
USPC .......................... 73/31.05; 324/699

(58) Field of Classification Search
USPC ............... 73/335.02, 335.03, 335.05, 335.06, 73/335.07, 335.11, 73, 23.3, 23.34, 29.01, 73/29.02, 31.05; 324/699
See application file for complete search history.

(56) References Cited

U.S. PATENT DOCUMENTS

| | | | |
|---|---|---|---|
| 4,442,422 A | 4/1984 | Murata et al. | |
| 5,571,401 A | 11/1996 | Lewis et al. | |
| 5,698,089 A | 12/1997 | Lewis et al. | |
| 6,807,842 B2 * | 10/2004 | Williams et al. | 73/23.2 |
| 6,902,701 B1 | 6/2005 | Hughes et al. | |

FOREIGN PATENT DOCUMENTS

| | | |
|---|---|---|
| JP | 5-312746 | 11/1993 |
| JP | 7-12767 | 1/1995 |
| JP | 07-318524 A | 12/1995 |
| JP | 11-503231 | 3/1999 |
| JP | 2006-10703 | 1/2006 |
| WO | WO 96/30750 | 10/1996 |
| WO | WO 99/53328 | 10/1999 |
| WO | WO 01/91202 | 11/2001 |
| WO | WO 03/089915 | 10/2003 |

\* cited by examiner

*Primary Examiner* — Peter Macchiarolo
*Assistant Examiner* — Jamar Ray
(74) *Attorney, Agent, or Firm* — Jean C. Edwards, Esq.; Edwards Neils PLLC

(57) ABSTRACT

A substance detection sensor includes an insulating layer; two electrodes spaced in opposed relation to each other on the insulating layer; and conductive layers formed between the two electrodes on the insulating layer so as to electrically connect the two electrodes, and of which a swelling ratio varies depending on the type and/or amount of a specific gas. The conductive layers are formed by dividing into plural layers between the two electrodes.

1 Claim, 10 Drawing Sheets

FIG. 3
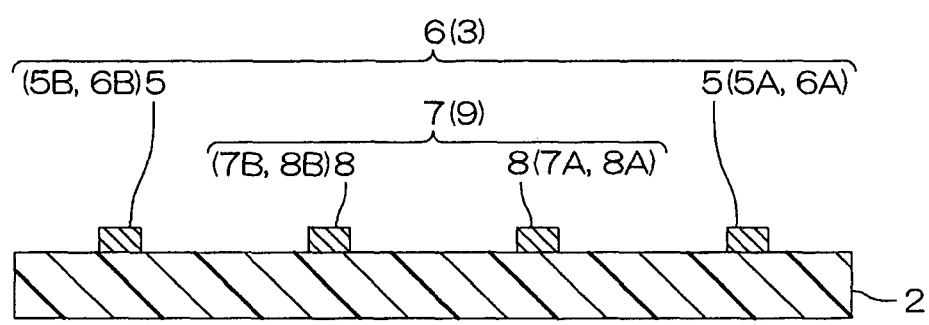
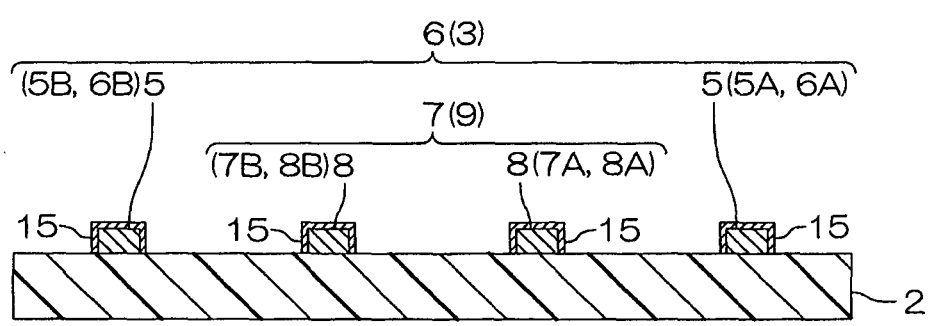
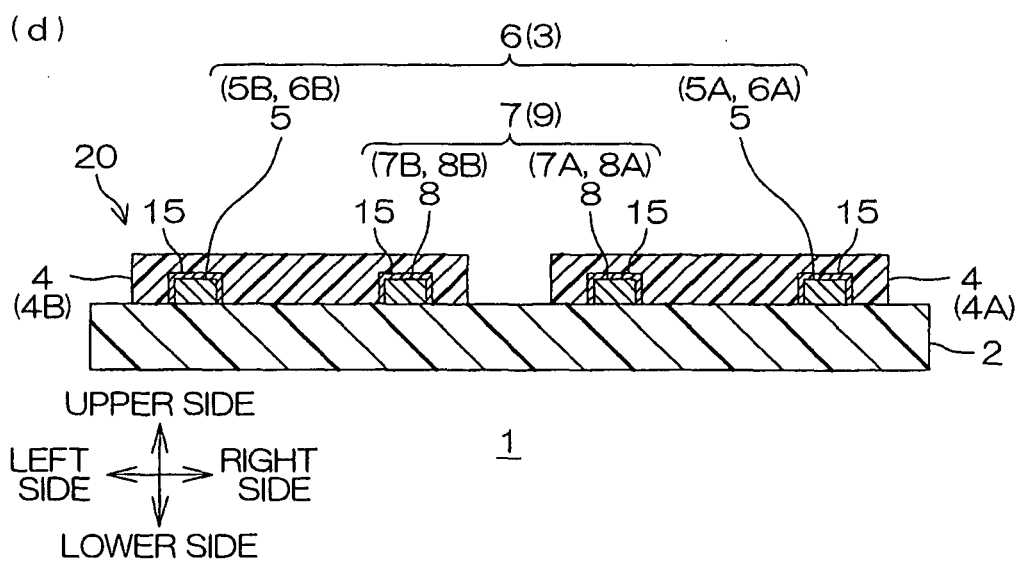

SUBSTANCE DETECTION SENSOR

CROSS REFERENCE TO RELATED APPLICATION

This application claims priority from Japanese Patent Application No. 2009-5091, filed Jan. 13, 2009, the content of which is herein incorporated by reference in its entirety.

BACKGROUND OF THE INVENTION

1. Field of the Invention

The present invention relates to a substance detection sensor, and more particularly to a substance detection sensor for mainly detecting the type or amount of gas.

2. Description of Related Art

Heretofore, material sensors for detecting gas or liquid have been used in various industrial applications. The material sensor is used for qualitative and quantitative analysis of specific gases or liquids.

For example, there have been proposed sensor arrays including a resistor containing a conductive substance, and first and second conductive leads spaced apart from each other and electrically coupled via the resistor (cf. Japanese Unexamined Patent Publication No. 2006-10703).

In the sensor arrays of Japanese Unexamined Patent Publication No. 2006-10703, the resistor is formed by applying (casting) a solution containing a conductive substance so as to contact the first and the second conductive leads, and then drying the solution.

SUMMARY OF THE INVENTION

However, in Japanese Unexamined Patent Publication No. 2006-10703, since the solution is applied onto the first and the second conductive leads to collectively form the resistor at a time, the resistor may be formed in uneven thickness. In particular, when the resistor is formed to have a large area, it may have a considerably uneven thickness.

As a result, the sensor cannot accurately detect a substance due to the uneven thickness of the resistor.

It is an object of the present invention to provide a substance detection sensor capable of detecting a substance with excellent accuracy by forming a conductive layer in uniform thickness.

The substance detection sensor of the present invention includes an insulating layer; two electrodes spaced in opposed relation to each other on the insulating layer; and a conductive layer formed between the two electrodes on the insulating layer so as to electrically connect the two electrodes, and of which a swelling ratio varies depending on the type and/or amount of a specific gas, the conductive layer being formed by dividing into plural layers between the two electrodes.

According to the substance detection sensor of the present invention, the conductive layers are formed by dividing a layer into plural layers, so that each of the conductive layers has a small area. This allows the thickness of the respective conductive layers to be made uniform. Therefore, the thickness of the entire conductive layer can be made uniform.

As a result, the substance detection sensor can detect a substance with excellent accuracy.

It is preferable that the substance detection sensor of the present invention includes wires for connecting the conductive layers formed by dividing into plural layers, and it is further preferable that the conductive layers formed by dividing into plural layers are spaced apart from each other, and the wires are connected to the respective adjacent conductive layers, or it is preferable that the conductive layers formed by dividing into plural layers include an overlapping portion overlapped each other, and the wires are connected to the respective adjacent conductive layers so as to sandwich the overlapping portion.

In the substance detection sensor, since the conductive layers formed by dividing a layer into plural layers and spaced apart from each other are connected between a pair of electrodes through the wires, the connection between the pair of electrodes can be ensured, which in turn can reliably perform substance detection with high accuracy.

Alternatively, in the substance detection sensor, since the conductive layers formed by dividing a layer into plural layers and including the overlapping portion is connected between the pair of electrodes through the wires, the connection between the pair of electrodes can be ensured, which in turn can reliably perform substance detection with high accuracy.

BRIEF DESCRIPTION OF THE DRAWINGS

FIG. 3 is a process diagram showing a method for producing the gas detection sensor shown in FIG. 2;
(a) showing the step of preparing an insulating layer,
(b) showing the step of forming an electrode pattern and a bridge wire,
(c) showing the step of forming a protective layer, and
(d) showing the step of forming conductive layers;

DETAILED DESCRIPTION OF PREFERRED EMBODIMENTS

Figure 1:
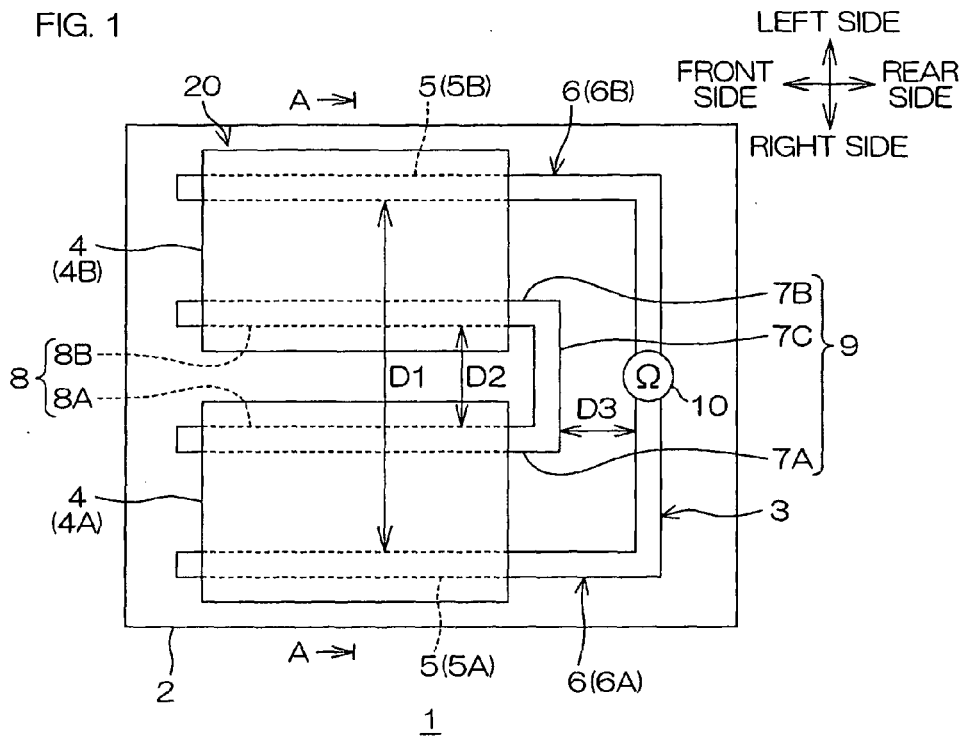
FIG. 1 is a plan view of a gas detection sensor as an embodiment of a substance detection sensor according to the present invention.
Figure 2:
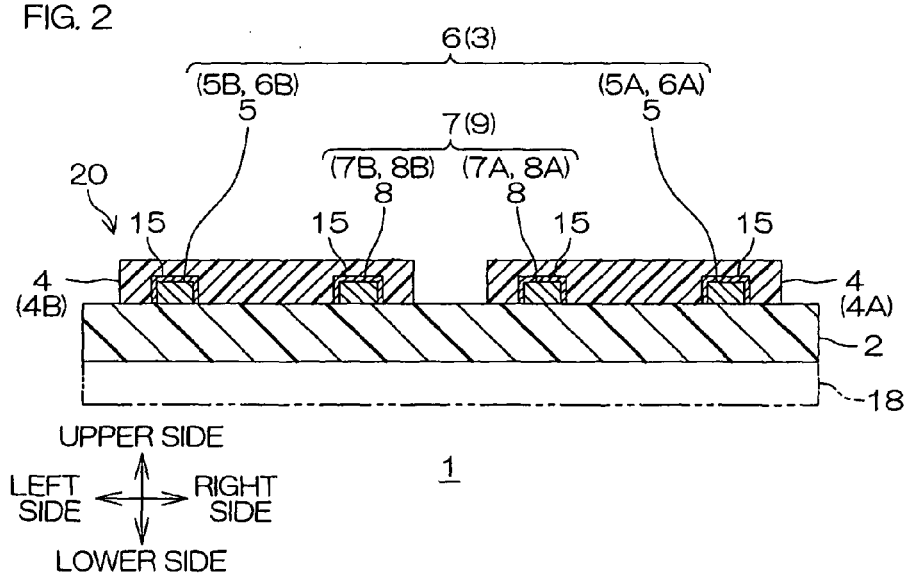
FIG. 2 is a sectional view taken along the line A-A of FIG. 1.

FIG. 1 is a plan view of a gas detection sensor as an embodiment of a substance detection sensor according to the present invention, FIG. 2 is a sectional view taken along the line A-A of FIG. 1, and FIG. 3 is a process diagram showing a method for producing the gas detection sensor shown in FIG. 2. Incidentally, the directions are described with reference to FIG. 1, that is, the left side, the right side, the lower side, the upper side, the near side, and the far side of the paper plane will be referred to as the "front side", "rear side", "right side" (one side), "left side" (the other side), "upper side", and "lower side", respectively.

In FIGS. 1 and 2, the gas detection sensor 1 includes an insulating layer 2, an electrode pattern 3 formed on the insulating layer 2, a bridge wire 9 serving as wiring formed on the insulating layer 2, and a conductive layer 4 formed on the insulating layer 2 so as to be electrically connected with the electrode pattern 3 and the bridge wire 9.

The insulating layer 2 is formed, for example, from a sheet having a generally rectangular shape in plane view.

The electrode pattern 3 includes a pair of electrode wires 6 on the upper surface of the insulating layer 2. The pair of electrode wires 6 is spaced in opposed relation to each other in the left-and-right direction, extends in the front-and-rear direction, and is formed in a wired circuit pattern (conductive pattern) in which each of the rear end portions thereof is bent inward in a direction opposed to each other.

Specifically, the pair of electrode wires 6 include a first wire (right-side wire) 6A arranged on the right side (one side in the left-and-right direction) and a second wire (left-side wire) 6B arranged in spaced relation on the left side of the first electrode wire 6A (the other side in the left-and-right direction). The rear end portions of the pair of electrode wires 6 are connected with an electrical resistance detector 10.

The bridge wire 9 is provided in order to connect the conductive layer 4, and, on the upper surface of the insulating layer 2, the bridge wire 9 is provided on the inner sides of the pair of electrode wires 6 in the opposed direction. Specifically, the bridge wire 9 is arranged on the inner sides of the pair of electrode wires 6 in the opposed direction in spaced relation thereto and formed in a generally U-shape in plane view opening toward the front side.

More particularly, the bridge wire 9 integrally includes a first connecting wire (right-side connecting wire) 7A arranged on the right side (one side in the left-and-right direction), a second connecting wire (left-side connecting wire) 7B arranged in spaced relation on the left side of the first connecting wire 7A (the other side in the left-and-right direction), and a third connecting wire (rear-side connecting wire) 7C for connecting the rear end portions thereof.

A protective layer 15 which covers the electrode pattern 3 and the bridge wire 9 is formed thereon.

The protective layer 15 is directly formed on the surfaces (the upper and side surfaces) of the electrode pattern 3 and the bridge wire 9.

The conductive layers 4 are formed by dividing a layer into plural (two) layers and are spaced apart from each other in the left-and-right direction. Each of the conductive layers 4 is formed in a generally rectangular shape in plane view extending in the front-and-rear direction, and includes a first conductive layer 4A arranged on the right side (one side in the left-and-right direction) and a second conductive layer 4B arranged in spaced relation on the left side of the first conductive layer 4A (the other side in the left-and-right direction).

The first conductive layer 4A is provided over the first electrode wire 6A and the first connecting wire 7A and covering them. The second conductive layer 4B is also provided over the second electrode wire 6B and the second connecting wire 7B and covering them.

The conductive layers 4, and the electrode pattern 3 and the bridge wire 9 that are covered with the conductive layers 4 constitute a detection portion 20 for detecting a specific gas in the gas detection sensor 1.

In the detection portion 20, the electrode wire 6 (the first electrode wire 6A or the second electrode wire 6B) of the electrode pattern 3 covered with the conductive layers 4 is determined as an electrode 5 (a first electrode 5A or a second electrode 5B), and the bridge wire 9 (the first connecting wire 7A or the second connecting wire 7B) covered with each of the conductive layers 4 is determined as a connecting portion 8 (a first connecting portion 8A or a second connecting portion 8B).

The electrode 5 and the connecting portion 8 are arranged in both end portions of the respective conductive layers 4 in the left-and-right direction. Specifically, the first electrode 5A and the first connecting portion 8A are arranged in the right side end portion and the left side end portion of the first conductive layer 4A, respectively, while the second connecting portion 8B and the second electrode 5B are arranged in the right side end portion and the left side end portion of the second conductive layer 4B, respectively.

That is, the first conductive layer 4A is connected to the first electrode 5A and the first connecting portion 8A, and the second conductive layer 4B is connected to the second electrode 5B and the second connecting portion 8B.

Thus, the conductive layers 4 (the first conductive layer 4A and the second conductive layer 4B) are electrically connected with the first electrode 5A and the second electrode 5B through the bridge wire 9 between the first electrode 5A and the second electrode 5B.

Next, a method for producing the gas detection sensor 1 is described with reference to FIG. 3.

In this method, an insulating layer 2 is first prepared, as shown in FIG. 3(a).

As an insulating material for forming the insulating layer 2, for example, synthetic resin such as a liquid crystal polymer (LCP; a polymer of an aromatic or aliphatic dihydroxy compound, a polymer of an aromatic or aliphatic dicarboxylic acid, a polymer of an aromatic hydroxycarboxylic acid, a polymer of an aromatic diamine, an aromatic hydroxyamine, or an aromatic aminocarboxylic acid, etc.), polyethylene terephthalate (PET), polyimide (PI), polyether nitril, polyether sulfone, polyethylene naphthalate, polyphenylene sulfide (PPS), polyether imide (PEI), and polyvinyl chloride is used. These insulating layers can be used alone or in combination.

As such insulating material, a material having a low coefficient of water absorption, humidity expansion, thermal expansion, and gas permeability is preferably used.

Among them, a liquid crystal polymer or polyethylene terephthalate is preferably used. Since a liquid crystal polymer or polyethylene terephthalate has a low coefficient of water absorption and gas permeability (oxygen permeability, etc.), the insulating layer 2 can be prevented from swelling due to absorption of water vapor in the ambient air, and the conductive layers 4 can be prevented from being affected due to penetrating of gas or water vapor from the undersurface of the insulating layer 2. Therefore, a detection error caused by the swelling of the insulating layer 2 and a detection error caused by the affection due to the penetration from the insulating layer 2 can be prevented.

To prepare the insulating layer 2, for example, a sheet of the above-mentioned insulating material is prepared. Alternatively, the insulating layer 2 can be prepared by forming a film of a varnish of an insulating material on a stripping plate, which is not shown, by casting, drying the film, and then curing the dried film as required.

Commercially available products can be used as the sheet of the above-mentioned insulating material, and, examples thereof include a VECSTAR series sheet (a liquid crystal polymer sheet, manufactured by Kuraray Co., Ltd.), a BIAC series sheet (a liquid crystal polymer sheet, manufactured by JAPAN GORE-TEX INC.), and a Lumirror series sheet (a polyethylene terephthalate sheet, manufactured by Toray Industries, Inc.).

The insulating layer 2 thus formed has a thickness in the range of, for example, 5 to 30 μm, or preferably 5 to 25 μm.

Subsequently, in this method, as shown in FIG. 3(b), an electrode pattern 3 and a bridge wire 9 are simultaneously formed on the insulating layer 2.

As a material for forming the electrode pattern 3 and the bridge wire 9, for example, a conductive material such as copper, nickel, gold, tin, rhodium, solder, or alloys thereof is used. Among them, copper is preferably used from the viewpoint of conductivity and processability.

The electrode pattern 3 and the bridge wire 9 are formed in the form of the above-mentioned pattern by a known patterning method such as a printing method, an additive method, or a subtractive method.

In the printing method, for example, a paste containing microparticles of the above-mentioned material is screen-printed on the upper surface of the insulating layer 2 in the above-mentioned pattern and then sintered. This directly forms the electrode pattern 3 and the bridge wire 9 on the upper surface of the insulating layer 2.

In the additive method, for example, a thin conductive film (a seed layer), which is not shown, is first formed on the upper surface of the insulating layer 2. The thin conductive film is formed by sequentially laminating a thin chromium film and a thin copper film by sputtering, or preferably chromium sputtering and copper sputtering.

A plating resist is then formed on the upper surface of the thin conductive film in a pattern reverse to the pattern of the electrode pattern 3 and the bridge wire 9, and the electrode pattern 3 and the bridge wire 9 are formed on the upper surface of the thin conductive film exposed from the plating resist by electrolytic plating. Thereafter, the plating resist and the thin conductive film in the portion on which the plating resist has been laminated are removed.

In the subtractive method, for example, a two-layer substrate (copper foil two-layer substrate, etc.) on which a conductive layer made of the above-mentioned conductive material is preliminarily laminated on the upper surface of the insulating layer 2 is first prepared, and a dry film resist is then laminated on the conductive layer. Thereafter, the dry film resist is exposed to light and developed. Then, an etching resist having the same pattern as the above-mentioned pattern of the electrode pattern 3 and the bridge wire 9 is formed. Subsequently, the conductive layer exposed from the etching resist is subjected to chemical etching (wet etching), and the etching resist is then removed to form the electrode pattern 3 and the bridge wire 9. To prepare the two-layer substrate, a known adhesive layer may be interposed between the insulating layer 2 and the conductive layer as required.

In the formation of the electrode pattern 3 and the bridge wire 9 by the above-mentioned subtractive method, commercially available products can be used as the copper foil two-layer substrate, and, for example, a liquid crystal polymer copper-clad laminate (ESPANEX L series, single-sided, standard type/P type, manufactured by Nippon Steel Chemical Co., Ltd.) in which a conductive layer made of copper is preliminarily laminated on the upper surface of the insulating layer 2 made of liquid crystal polymer is used.

Among these patterning methods, a printing method is preferably used. This method ensures that the electrode pattern 3 and the bridge wire 9 can be directly formed on the upper surface of the insulating layer 2, so that a specific gas can be detected with high accuracy.

The electrode pattern 3 and the bridge wire 9 thus formed have a thickness in the range of, for example, 5 to 30 μm, or preferably 5 to 20 μm.

An electrode wire 6 has a length (length of a first electrode wire 6A and a second electrode wire 6B in the front-and-rear direction) in the range of, for example, 5 to 100 mm, or preferably 5 to 50 mm, and the bridge wire 9 has a length (length of a first connecting wire 7A and a second connecting wire 7B in the front-and-rear direction) in the range of, for example, 4.5 to 95.0 mm, or preferably 4.5 to 45.0 mm.

The electrode wire 6 has a width (length of the first electrode wire 6A and the second electrode wire 6B in the left-and-right direction) in the range of, for example, 10 to 500 μm, or preferably 20 to 300 μm. A spacing D1 (spacing in the left-and-right direction) between the electrode wires 6 is appropriately selected according to the number of conductive layers 4 and its width, and is in the range of, for example, 1 to 30 mm, or preferably 2 to 10 mm.

The bridge wire 9 has a width (length of the first connecting wire 7A and the second connecting wire 7B in the left-and-right direction, and length of a third connecting wire 7C in the front-and-rear direction) in the range of, for example, 10 to 500 μm, or preferably 20 to 300 μm. A spacing D2 between the first connecting wire 7A and the second connecting wire 7B is in the range of, for example, 0.5 to 10 mm, or preferably 1 to 5 mm.

The spacing between the electrode pattern 3 and the bridge wire 9 in the left-and-right direction, specifically, the spacing between the first electrode wire 6A and the first connecting wire 7A, and the spacing between the second electrode wire 6B and the second connecting wire 7B are determined by the spacing D1 between the electrode wires 6, the width of the first connecting wire 7A and the second connecting wire 7B, and the spacing D2 therebetween.

A spacing D3 (spacing in the front-and-rear direction) between the rear end portion (bending portion) of the electrode wire 6 and the bridge wire 9 (the third connecting wire 7C) is in the range of, for example, 0.5 to 10 mm, or preferably 1 to 5 mm.

The formation of the electrode pattern 3 and the bridge wire 9 simultaneously forms a pair of electrodes 5 in the electrode pattern 3 and a pair of connecting portions 8 in the bridge wire 9.

Subsequently, in this method, as shown in FIG. 3(c), a protective layer 15 is formed so as to cover the electrode pattern 3 and the bridge wire 9.

As a material for forming the protective layer 15, a metal material such as gold is used. When the protective layer 15 is formed of a metal material, even if a specific gas to be detected is acid gas, this protective layer 15 can reliably prevent the electrode pattern 3 and the bridge wire 9 from corrosion.

The protective layer 15 is formed by a known thin film forming method, such as sputtering and plating such as electroless plating or electrolytic plating, so as to cover the electrode pattern 3 and the bridge wire 9.

The protective layer 15 thus formed has a thickness in the range of, for example, 0.05 to 3 μm, or preferably 0.5 to 1.5 μm.

Subsequently, in this method, as shown in FIG. 3(d), the conductive layers 4 are sequentially formed on the insulating layer 2 by dividing a layer into plural layers so as to cover the protective layer 15.

Specifically, the first conductive layer 4A is formed on the insulating layer 2 so as to cover the protective layer 15 corresponding to the first electrode 5A and the first connecting portion 8A, and subsequently, the second conductive layer 4B is formed on the insulating layer 2 so as to cover the protective layer 15 corresponding to the second electrode 5B and the second connecting portion 8B.

The conductive layers 4 are formed from a conductive material which is formed from, for example, a mixture of a conductive particle exhibiting conductivity and a non-conductive substance which swells according to the type and amount (concentration) of a specific gas.

The conductive particle that may be used includes, for example, an organic conductor, an inorganic conductor, or a mixed organic/inorganic conductor.

Examples of the organic conductor include conductive polymers such as polyaniline, polythiophene, polypyrrole, and polyacetylene; carbonaceous materials such as carbon blacks, graphite, corks, and C60; and charge transfer complexes such as tetramethylparaphenylenediamine-chloranile, alkali metal tetracyanoquinolinodimethane complexes, and tetrathiofulvalene halide complexes.

Examples of the inorganic conductor include metals such as silver, gold, copper, and platinum; alloys of the above-mentioned metals such as Au—Cu alloys; highly doped semiconductors such as silicon, gallium arsenide (GaAs), indium phosphide (InP), molybdenum sulfide ($MoS_2$), and titanium oxide ($TiO_2$); conductive metal oxides such as indium oxide ($In_2O_3$), tin oxide ($SnO_2$), and sodium platinum oxide ($NaxPt_3O_4$); and superconductors such as $YBa_2Cu_3O_7$ and $Tl_2Ba_2Ca_2Cu_3O_{10}$.

Examples of the mixed organic/inorganic conductor include tetracyano-platinate complexes, iridium-halocarbonyl complexes, and stacked macrocyclic complexes.

These conductive particles can be used alone or in combination.

The non-conductive substance that may be used includes, for example, non-conductive organic polymers such as main chain carbon polymers, main chain acyclic heteroatom polymers, and main chain heterocyclic polymers.

Examples of the main chain carbon polymer include polydiene, polyalkene, polyacrylic, polymethacrylic, polyvinyl ether, polyvinyl thioether, polyvinyl alcohol, polyvinyl ketone, polyvinyl halide, polyvinyl nitrile, polyvinyl ester, polystyrene, poly (α-methylstyrene), polyarylene, polyvinyl alcohol, and polyvinyl acetate.

Examples of the main chain acyclic heteroatom polymer include polyoxide, polycarbonate, polyester, polyanhydride, polyurethane, polysulfonate, polysiloxane, polysulfide, polythioester, polysulfone, polysulfone amide, polyamide, polyamide amine (polyamide amine dendrimer), polyurea, polyphosphazene, polysilane, and polysilazane.

Examples of the main chain heterocyclic polymer includes poly(furan tetracarboxylic acid diimides), polybenzoxazoles, polyoxadiazoles, polybenzothiadinophenothiazines, polybenzothiazoles, polypyrazinoquinoxalines, polypyromellitimides, polyquinoxalines, polybenzimidazoles, polyoxindoles, polyoxoisoindolines, polydioxoisoindolines, polytriazines, polypyridazines, polypiperazines, polypyridines, polypiperidines, polytriazoles, polypyrazoles, polypyrrolidines, polycarboranes, polyoxabicyclononanes, polydibenzofurans, polyphthalides, polyacetals, polyvinyl pyrrolidones, and polybisphenols, or other hydrocarbons.

As the non-conductive substance, for example, oligomers such as polyester acrylate oligomer may also be used.

These non-conductive substances can be used alone or in combination.

To form the conductive layer 4, a coating method such as spraying by an ultrasonic spray method, solution casting, air spraying, or drop coating, is used. Further, for example, a thin-film forming technique such as vacuum vapor deposition, CVD, plasma polymerization, ionized cluster beam deposition, epitaxial growth, and Langmuir Blodgett (LB) is used.

Preferably, spraying by an ultrasonic spray method is used.

In the spraying by an ultrasonic spray method, a conductive component-containing liquid (solution and/or suspension) containing an organic solvent, a conductive particle, and a non-conductive substance (or precursors (monomers) thereof) is prepared and then sprayed onto the insulating layer 2 by an ultrasonic spray method.

The organic solvent having a boiling point of 40 to 120° C. is preferable, and examples thereof include ketones such as acetone, methyl ethyl ketone, and methyl isobutyl ketone; alcohols such as methyl alcohol, ethyl alcohol, isopropyl alcohol, and n-propyl alcohol; aromatic hydrocarbons such as toluene and xylene; halogenated hydrocarbons such as a methylene chloride; ethers such as tetrahydrofuran (THF); and nitriles such as acetonitrile.

These organic solvents can be used alone or in combination.

In the case of preparing the conductive component-containing liquid as a solution, an organic solvent (solvent) capable of dissolving a conductive particle and a non-conductive substance (or precursors thereof) is selected as the organic solvent, and such organic solvent is mixed with the conductive particle and the non-conductive substance (or the precursors thereof) to be dissolved.

Alternatively, in the case of preparing the conductive component-containing liquid as a suspension, an organic solvent (dispersion medium) capable of dispersing a conductive particle is selected as the organic solvent, and the conductive particle is suspended in the organic solvent. In such case, for example, the conductive particle is suspended in the organic solvent with a known agitator such as a forced agitator or an ultrasonic agitator.

As for the mixing proportions of the respective ingredients to prepare the conductive component-containing liquid, per 100 parts by weight of the non-conductive substance, the conductive particle is in the range of, for example, 10 to 50 parts by weight, or preferably 20 to 35 parts by weight, and the organic solvent is in the range of, for example, 2000 to 20000 parts by weight, or preferably 5000 to 15000 parts by weight.

If desired, known additives such as a catalyst may be added to the conductive component-containing liquid.

The conductive component-containing liquid thus prepared has a viscosity (at 25° C.) in the range of, for example, $1\times10^{-4}$ to 0.05 Pa·s, or preferably $5\times10^{-4}$ to 0.01 Pa·s.

The ultrasonic spray method is a spray coating method using an ultrasonic wave, for example, in which a liquid is sprayed in the form of a liquid droplet (in mist form) having a fine particle diameter by ultrasonic vibration. Thus, a coating solution can be applied to an object uniformly and effectively.

When the conductive component-containing liquid is sprayed onto the insulating layer 2 by an ultrasonic spray method, it is sprayed in the form of a liquid droplet having a fine particle diameter. Therefore, the organic solvent in the conductive component-containing liquid evaporates by the time when the liquid droplet of the conductive component-containing liquid reaches the insulating layer 2. For this reason, such ultrasonic spray method can suppress wetting and spreading of the conductive component-containing liquid. As a result, agglomeration and/or uneven distribution of the conductive material (conductive particle and non-conductive substance) can be suppressed.

In the spraying of the conductive component-containing liquid by the ultrasonic spray method, the frequency of the ultrasonic wave is in the range of, for example, 20 to 150 kHz, or preferably 60 to 120 kHz. When the frequency of the ultrasonic wave is within the above-mentioned range, the sprayed conductive component-containing liquid can have an extremely finer diameter than the liquid droplet obtained by an air spray method.

More specifically, for example, the use of an ultrasonic wave having a frequency of 60 kHz can make the particle diameter of the conductive component-containing liquid approximately 35 μm or less while the use of an ultrasonic wave having a frequency of 120 kHz can make the particle diameter of the conductive component-containing liquid approximately 20 μm or less.

The finer diameter the liquid droplet of the conductive component-containing liquid has, the more uniformly the conductive component-containing liquid can be sprayed onto the insulating layer 2, so that the thickness of the conductive layer 4 thus obtained can be made more uniform.

Commercially available ultrasonic spray devices can be used to spray the above-mentioned conductive component-containing liquid onto the insulating layer 2 by the ultrasonic spray method. As such ultrasonic spray device, for example, an ultrasonic spray nozzle (manufactured by Sono-Tek Corporation) is used.

To spray the conductive component-containing liquid onto the insulating layer 2, more specifically, for example, an ultrasonic spray device is first installed so that its jet opening faces the insulating layer 2, and the conductive component-containing liquid is then sprayed from the jet opening of the ultrasonic spray device onto the insulating layer 2 that is, for example, 10 to 200 mm, or preferably 30 to 100 mm spaced apart from the jet opening thereof.

Such spraying allows the organic solvent in the conductive component-containing liquid to well evaporate by the time a jet of the conductive component-containing liquid injected from the jet opening reaches the insulating layer 2.

In such spraying of the conductive component-containing liquid, when the conductive component-containing liquid freely falls as a liquid droplet having a fine particle diameter, for example, assist gas can be introduced as required.

Examples of the assist gas include nitrogen, argon, and air, and when the nozzle has a diameter of approximately 1 mm, the discharge pressure thereof is in the range of, for example, 0.05 to 5.0 kPa, or preferably 0.3 to 1.0 kPa.

For example, a mask may be used to spray the conductive component-containing liquid in a pattern corresponding to the respective conductive layers 4. More specifically, before the spraying of the conductive component-containing liquid, the insulating layer 2 is covered with a mask having an opening formed in a pattern corresponding to a first conductive layer 4A. Subsequently, the conductive component-containing liquid is sprayed from above of the insulating layer 2 and the mask onto the insulating layer 2 and the protective layer 15 both exposed from the opening in the mask, and the mask is then removed. Thus, the first conductive layer 4A is first formed.

Thereafter, the insulating layer 2 on which the first conductive layer 4A is formed is covered with a mask having an opening formed in a pattern corresponding to a second conductive layer 4B. Subsequently, the conductive component-containing liquid is sprayed from above of the insulating layer 2 and the mask onto the insulating layer 2 and the protective layer 15 both exposed from the opening in the mask, and the mask is then removed. Thus, the second conductive layer 4B is formed.

Therefore, the conductive component-containing liquid can be sequentially sprayed in the patterns corresponding to the respective conductive layers 4.

It should be noted that the conductive component-containing liquid is sprayed, for example, at room temperature (at approximately 25° C.).

In this way, the respective conductive layers 4 (the first and the second conductive layers 4A and 4B) can be sequentially formed by spraying the conductive component-containing liquid onto the insulating layer 2 plural times (twice) in sequence.

Here, generally, in the formation of the respective conductive layers 4, for example, when the conductive component-containing liquid is applied to the insulating layer 2 using a coating method such as solution casting, air spraying, or drop coating, the conductive component-containing liquid thus applied may wet-spread over the insulating layer 2 until it dries. In such case, agglomeration and uneven distribution of the conductive particles may occur during evaporation of the organic solvent in the conductive component-containing liquid, resulting in difficulty in uniformly forming the conductive layers 4 each having a predetermined thickness.

However, the spraying by the ultrasonic spray method allows the organic solvent to evaporate during the spraying. Therefore, wetting and spreading of the conductive component-containing liquid can be suppressed, so that the thickness of the respective conductive layers 4 can be made uniform.

Further, in the spraying by the ultrasonic spray method, since the conductive layers 4 are formed by spraying the conductive component-containing liquid, there is no significant loss of the conductive component-containing liquid, which is highly cost effective.

Conductivity may also be imparted to the conductive layers 4 formed in the above manner by doping (e.g., exposure to iodine) as required.

Each of the conductive layers 4 has a thickness in the range of, for example, 0.01 to 50 μm, preferably 0.1 to 20 μm, or more preferably 0.2 to 10 μm.

Further, each of the conductive layers 4 has a length (length in the front-and-rear-direction) in the range of, for example, 5 to 95 mm, or preferably 5 to 45 mm, and has a width (length in the left-and-right direction) in the range of, for example, 0.5 to 20 mm, preferably 1 to 5 mm. The spacing between the conductive layers 4 (the first and the second conductive layers 4A and 4B) is in the range of, for example, 0.5 to 10 mm, or preferably 1 to 5 mm. The first conductive layer 4A and the second conductive layer 4B have, for example, the same area, specifically, in the range of 2.5 to 1900 $mm^2$, or preferably 5 to 225 $mm^2$.

Thus, a detection portion 20 including the conductive layers 4, the electrodes 5, and the connecting portions 8 can be formed.

In the conductive layers 4 in the detection portion 20 thus formed, an electrical pathway (path) formed of conductive particles between the first electrode 5A and the first connecting portion 8A, and between the second electrode 5B and the second connecting portion 8B can suffer from electrical interference due to a gap formed of non-conductive substance. Such gap of the non-conductive substance provides a predetermined electrical resistance to between the first electrode 5A and the first connecting portion 8A, and between the second electrode 5B and the second connecting portion 8B (between the first and the second electrodes 5A and 5B), and the predetermined electrical resistance varies according to the swelling of the conductive layers 4 due to the absorption and adsorption of a specific gas to be described later.

In the detection portion 20, the type of the conductive layers 4 may be the same or different from each other. Further, the gas detection sensor 1 is formed as a wired circuit board because it includes the insulating layer 2 and an electrode pattern 3 (wired circuit pattern).

Thereafter, as shown in FIG. 1, the rear end portions of a pair of electrode wires 6 are connected to the electrical resistance detector 10. Thus, the gas detection sensor 1 can be produced.

Next, a method for detecting a specific gas using the gas detection sensor 1 will be described.

First, in this method, a gas detection sensor 1 is arranged in a location where a specific gas is desired to be detected.

The specific gas to be detected by the gas detection sensor 1 is not particularly limited, and examples thereof include organic substances such as alkane, alkene, alkyne, allene, alcohol, ether, ketone, aldehyde, carbonyl, and carbanion, derivatives (e.g., halogenated derivative, etc.) of the above-mentioned organic substances, biochemical molecules such as sugar, isoprene, isoprenoid, and chemical substances such as a fatty acid and derivatives of a fatty acid.

Thereafter, in this method, an electrical resistance between a first electrode 5A and a second electrode 5B in a detection portion 20 is detected by an electrical resistance detector 10. More specifically, when a specific gas contacts a non-conductive substance of conductive layers (conductive material) 4, the non-conductive substance absorbs or adsorbs the specific gas and then swells according to the type and/or amount (concentration) of the specific gas. This leads to swelling of the conductive layers 4, thereby changing the electrical resistance value between the first electrode 5A and the second electrode 5B in the conductive layers 4. Such change in the electrical resistance value is detected by the electrical resistance detector 10.

By analyzing the detected change in the electrical resistance value by a computer, which is not shown, having a given library, the specific gas is qualitatively and/or quantitatively analyzed for the type and/or amount (concentration) thereof.

These analyses for the change in the electrical resistance value can be performed according to the description of Japanese Unexamined Patent Publication No. 11-503231 or U.S. Pat. No. 5,571,401.

In the gas detection sensor 1, the type and amount of the specific gas can be reliably detected in the detection portion 20 by detecting the electrical resistance value in the conductive layer 4 of which the swelling ratio varies depending on the type and amount of the specific gas, by the electrical resistance detector 10.

The conductive layer 4 is formed by dividing into two layers, a first conductive layer 4A and a second conductive layer 4B. Therefore, each of the first conductive layer 4A and the second conductive layer 4B has a smaller area partitioned than the entire conductive layer 4, specifically, an area of one-half (½) of the total area of the first conductive layer 4A and the second conductive layer 4B. This partition can make the thickness of the first conductive layer 4A and the second conductive layer 4B even more uniform. Therefore, the thickness of the entire conductive layer 4 can be made uniform.

As a result, the type and amount (concentration) of the specific gas can be detected with excellent accuracy.

In the gas detection sensor 1, the first conductive layer 4A and the second conductive layer 4B, which are formed by dividing into two layers and spaced apart from each other, are connected with each other through the bridge wire 9 between the first electrode 5A and the second electrode 5B. Therefore, electrical connection between the first electrode 5A and the second electrode 5B can be reliably achieved, which in turn can reliably perform gas detection with high accuracy.

In the above explanation, the gas detection sensor 1 is exemplified and the specific substance to be detected is described as a gas. The gas detection sensor of the present invention does not limit the state of the substance to be detected and, for example, the specific substance to be detected may be a liquid.

In the above explanation, two detection portions 20 having two conductive layers 4 (the first and the second conductive layers 4A and 4B) are provided. However, the number of detection portions 20 is not particularly limited and, for example, three or more detection portions can be provided, though not shown. Such provision of the detection portions 20 can achieve detection of the type and amount (concentration) of a specific gas with even higher accuracy.

In the above explanation, in the formation of the conductive layers 4, the first conductive layer 4A and the second conductive layer 4B are sequentially formed. However, for example, they may be formed simultaneously. When the first conductive layer 4A and the second conductive layer 4B are simultaneously formed by spraying by an ultrasonic spray method, a conductive component-containing liquid is sprayed at once using a mask having two openings formed in a pattern corresponding to the first conductive layer 4A and the second conductive layer 4B.

In this method, the conductive layer 4 can be formed easily in a short time.

In the above explanation, the undersurface of the insulating layer 2 is exposed. However, for example, as shown in phantom line in FIG. 2, the undersurface of the insulating layer 2 can be covered with a metal layer 18.

The metal layer 18 is formed under the insulating layer 2, and more specifically, is provided over the entire undersurface of the insulating layer 2.

As a metal material for forming the metal layer 18, for example, stainless steel, 42-alloy, aluminum, copper-beryllium, or phosphor bronze is used. Preferably, stainless steel is used from the viewpoint of corrosion resistance.

To provide the metal layer 18, for example, the above-mentioned metal layer 18 is preliminarily prepared and then, the insulating layer 2 is formed. Alternatively, the metal layer 18 and the insulating layer 2 can be prepared as a two-layer substrate on which the metal layer 18 and the insulating layer 2 are preliminarily sequentially laminated. Further alternatively, they can be prepared as a three-layer substrate on which the metal layer 18, the insulating layer 2, and a conductive layer (a conductive layer for forming an electrode pattern 3 and a bridge wire 9) are preliminarily sequentially laminated. Commercially available products can be used as the three-layer substrate, and for example, a liquid crystal polymer copper-clad laminate (ESPANEX L series, double-sided, standard type/P type, manufactured by Nippon Steel Chemical Co., Ltd.) in which the insulating layer 2 made of liquid crystal polymer and the conductive layer made of copper are preliminarily laminated on the surface of the metal layer 18 made of copper is used.

The metal layer 18 has a thickness in the range of, for example, 0.05 to 50 µm, or preferably 0.1 to 20 µm.

When such metal layer 18 is provided under the insulating layer 2, particularly the insulating layer 2 made of insulating material having high gas permeability, the metal layer 18 can cut off the gas to be brought into contact with the insulating layer 2 from the underside, so that the insulating layer 2 can be prevented from swelling due to absorption of water vapor in the ambient air, and the conductive layer 4 can be prevented from being affected due to penetrating of gas and water vapor from the undersurface of the insulating layer 2. Therefore, a detection error caused by the swelling of the insulating layer 2 and a detection error caused by the affection due to the penetration from the insulating layer 2 can be prevented.

Further, in the above explanation, the protective layer 15 is formed so as to cover the electrode pattern 3 and the bridge wire 9. However, the protective layer 15 may be formed so as to cover only the electrodes 5 and the connecting portions 8 but not to cover the electrode wires 6 and the connecting wires 7 that are not included in the region of the detection portion 20.

Furthermore, in the above explanation, the protective layer 15 is formed. However, for example, although not shown, the electrodes 5 and the conductive layers 4 can be directly formed without forming the protective layer 15.

FIGS. 4 to 12 show another embodiment of the gas detection sensor according to the present invention. The same reference numerals are provided in the subsequent figures for members corresponding to each of those described above, and their detailed description is omitted.

In the above explanation, the conductive layer 4 is divided into two layers. However, the number of divisions is not particularly limited and, for example, it may be divided into three (see FIG. 4), or four or more layers.

Figure 4:
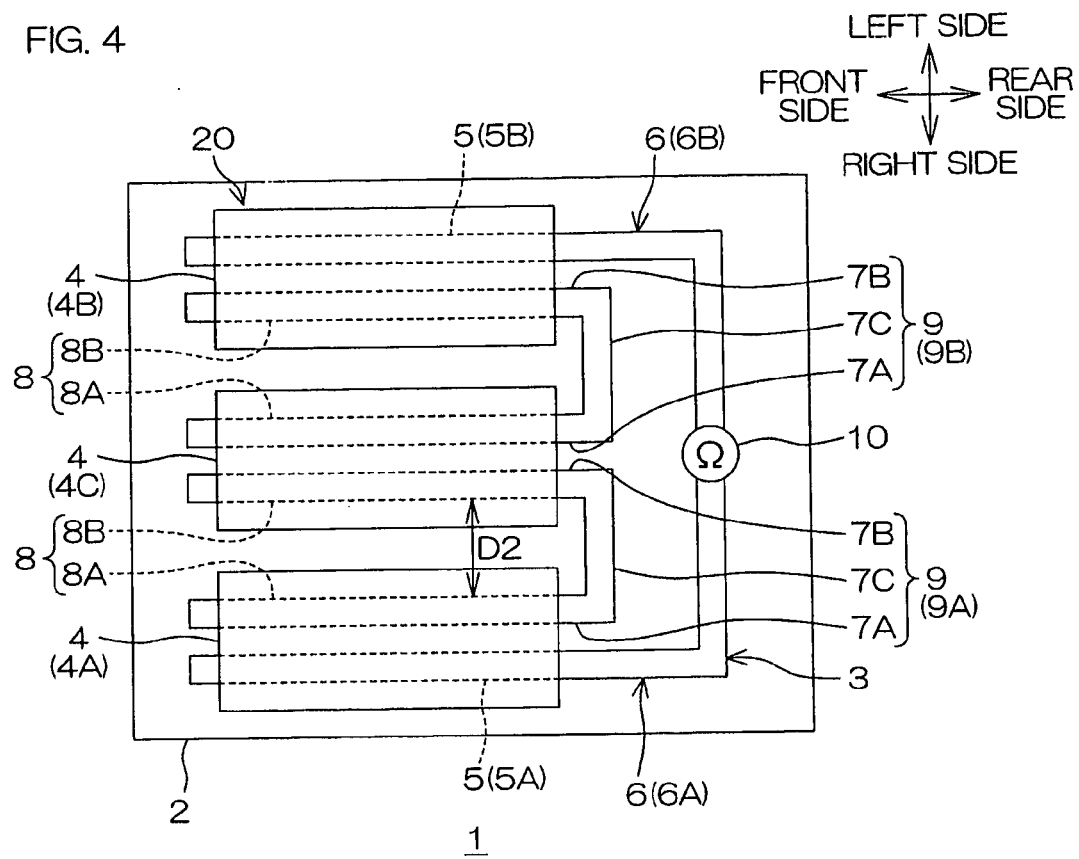
FIG. 4 is a plan view of another embodiment (an embodiment in which three conductive layers are provided) of the gas detection sensor according to the present invention.

In FIG. 4, the conductive layer 4 includes three conductive layers, that is, the first conductive layer 4A, the second conductive layer 4B, and the third conductive layer 4C, and the first conductive layer 4A, the third conductive layer 4C, and the second conductive layer 4B are sequentially arranged from the right side toward the left side.

Further, the bridge wire 9 includes the first bridge wire 9A connected to the first conductive layer 4A and the third conductive layer 4C, and the second bridge wire 9B connected to the third conductive layer 4C and the second conductive layer 4B.

Since each of the first, the second, and the third conductive layers 4A, 4B, and 4C that are formed by dividing into three layers as shown in FIG. 4 has a smaller area partitioned than each area of the first and the second conductive layers 4A and 4B shown in FIG. 1, specifically, an area of one-third (⅓) of the total area of the first, the second, and the third conductive layers 4A, 4B, and 4C, the first, the second, and the third conductive layers 4A, 4B, and 4C can have even more uniform thickness.

Therefore, the thickness of the entire conductive layer 4 can be made uniform. As a result, the type and amount (concentration) of the specific gas can be detected with even more excellent accuracy.

More particularly, the total area of the conductive layer 4 is preliminarily determined, and when such predetermined area is too large to easily make the thickness uniform, the number of divisions is set to be increased as described above. Along with this increase, the number of the bridge wire 9 is increased. Specifically, when the total area of the conductive layer 4 is, for example, 40 mm$^2$, the number of divisions is set to two or more, or when it is, for example, 60 mm$^2$, the number of divisions is set to three or more.

In the above explanation, the bridge wire 9 is formed in a generally U-shape in plane view. However, the shape thereof is not limited. For example, it can be formed in a generally rectangular shape in plane view (FIG. 5), in a generally rectangular frame shape in plane view (FIGS. 6 and 7), or in a generally H-shape in plane view (FIG. 8).

Figure 5:
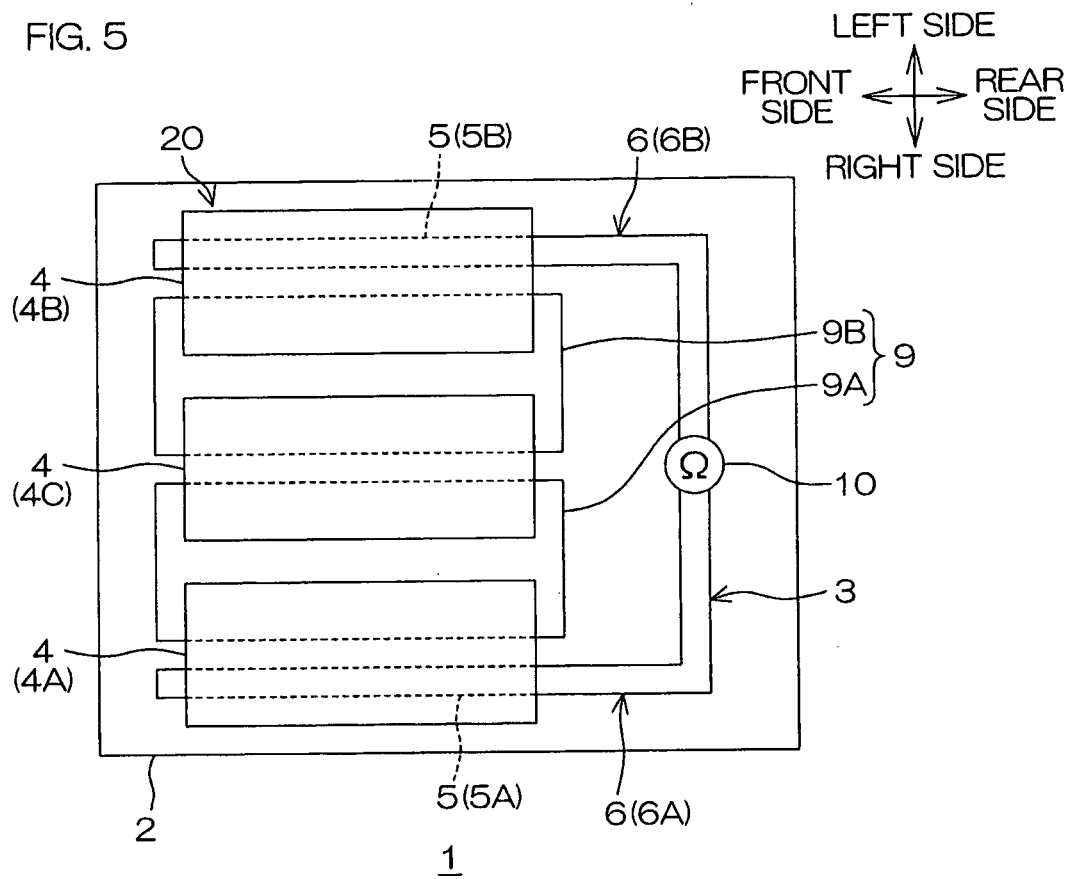
FIG. 5 is a plan view of another embodiment (an embodiment in which a bridge wire is formed in a generally rectangular shape in plane view) of the gas detection sensor according to the present invention.

In FIG. 5, the bridge wire 9 is formed in the shape of a thin flat sheet.

In the gas detection sensor 1, since the bridge wire 9 is formed in a flat plate shape, the resistance between the first conductive layer 4A and the second conductive layer 4B can be reduced. Moreover, the bridge wire 9 can effectively prevent a broken wire, thereby improving the yield of the gas detection sensor 1. Further, the bridge wire 9 having a flat plate shape can support the insulating layer 2, resulting in stabilization of the size of the gas detection sensor 1.

Figure 6:
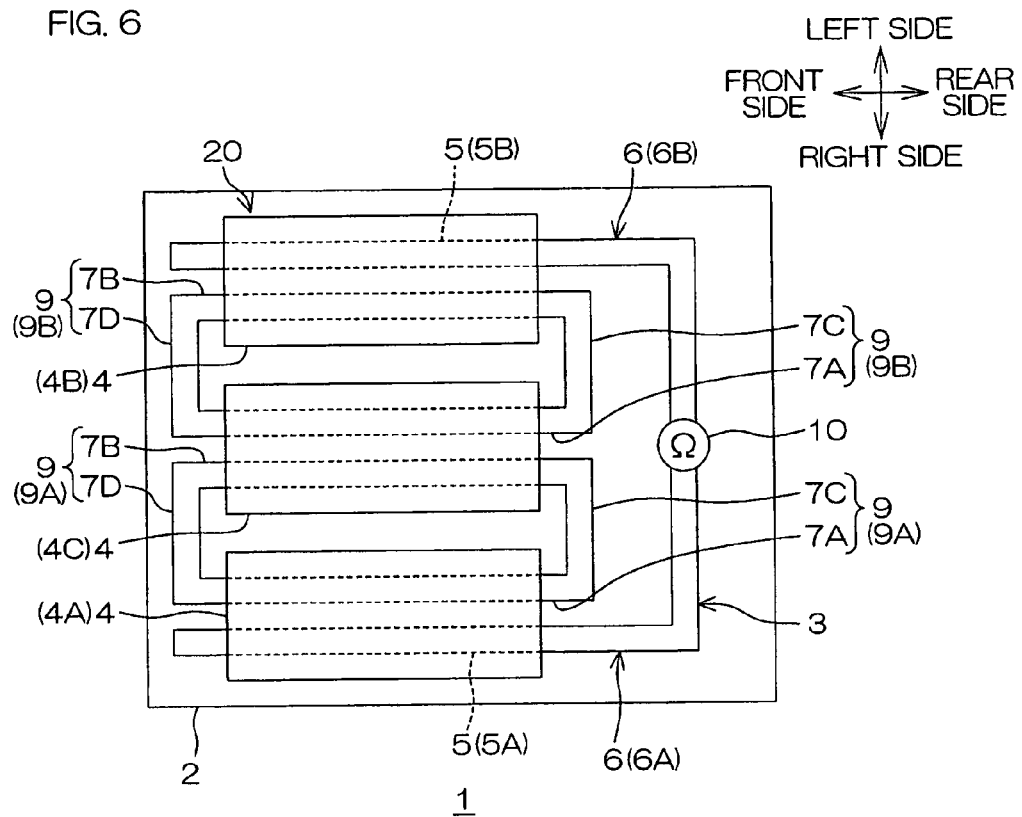
FIG. 6 is a plan view of another embodiment (an embodiment in which a bridge wire is formed in a generally rectangular frame shape in plane view) of the gas detection sensor according to the present invention.

In FIG. 6, the bridge wire 9 further includes a fourth connecting wire (a front-side connecting wire) 7D which connects between the front end portions of the first and the second connecting wires 7A and 7B.

Figure 7:
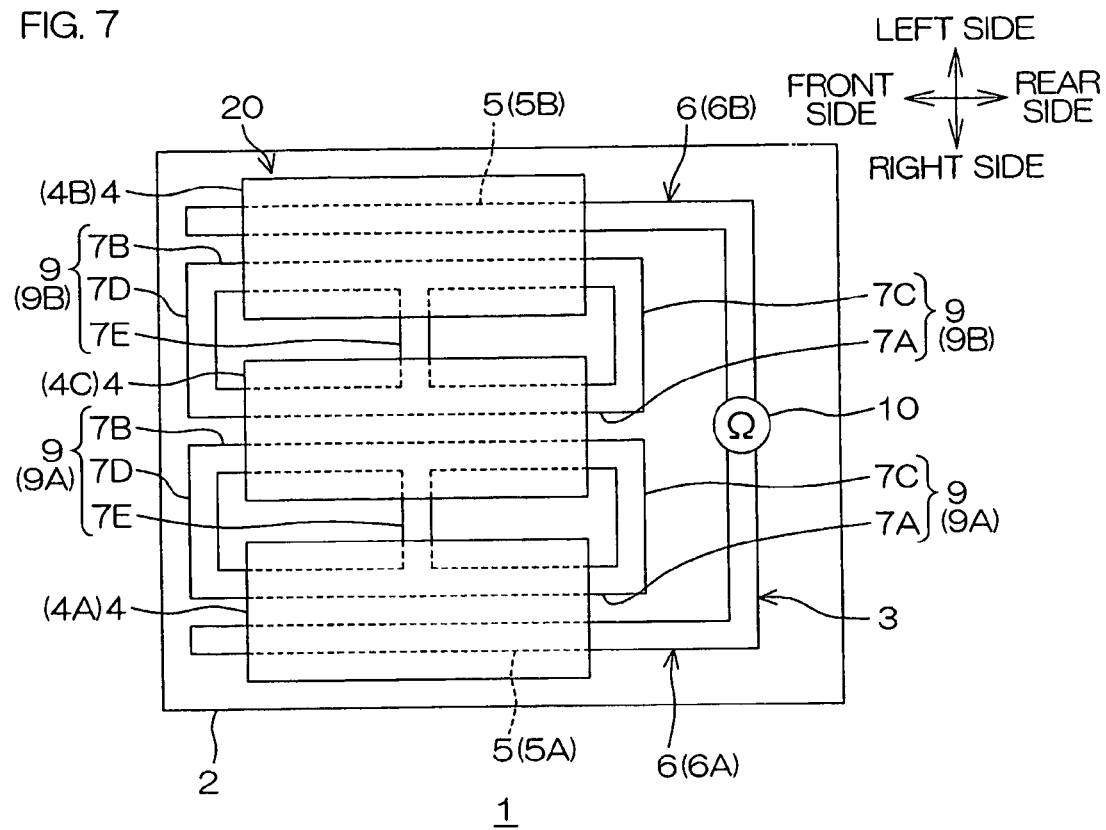
FIG. 7 is a plan view of another embodiment (an embodiment in which a bridge wire is formed in a generally rectangular frame shape in plane view) of the gas detection sensor according to the present invention.
Figure 8:
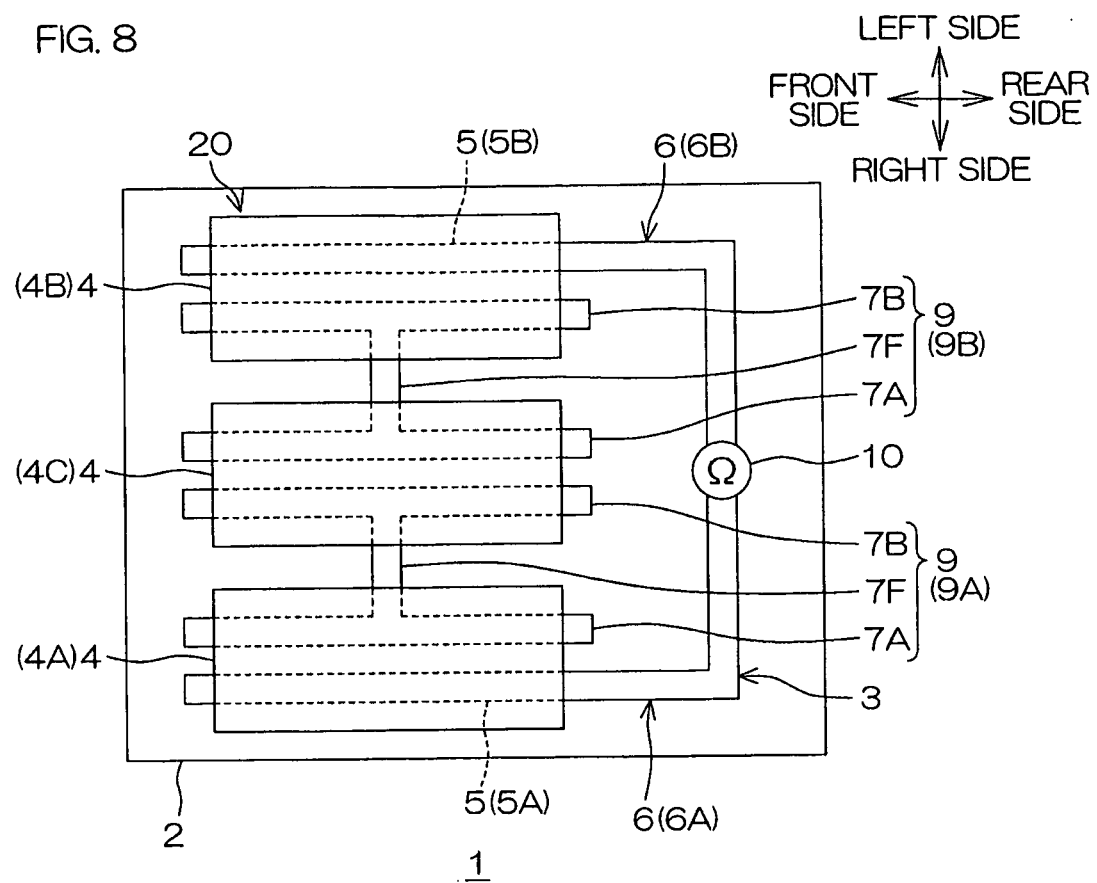
FIG. 8 is a plan view of another embodiment (an embodiment in which a bridge wire is formed in a generally H-shape in plane view) of the gas detection sensor according to the present invention.

In FIG. 7, the bridge wire 9 is formed in a generally H-shape in plane view opening toward both the front side and the rear side, and further includes a fifth connecting wire 7E which connects between the midpoints of the first and the second connecting wires 7A and 7B in the front-and-rear-direction. The fifth connecting wire 7E extends in the left-and-right direction.

In FIG. 8, the bridge wire 9 integrally includes the first connecting wire 7A, the second connecting wire 7B, and a sixth connecting wire (cross wire) 7F. The sixth connecting wire (cross wire) 7F connects between the midpoints of the first and the second connecting wires 7A and 7B in the front-and-rear-direction, and is formed so as to extend in the left-and-right direction.

In the above explanation, the bridge wire 9 is provided. However, for example, as shown in FIGS. 9 and 10, the first conductive layer 4A and the second conductive layer 4B can be connected without providing the bridge wire 9.

Figure 9:
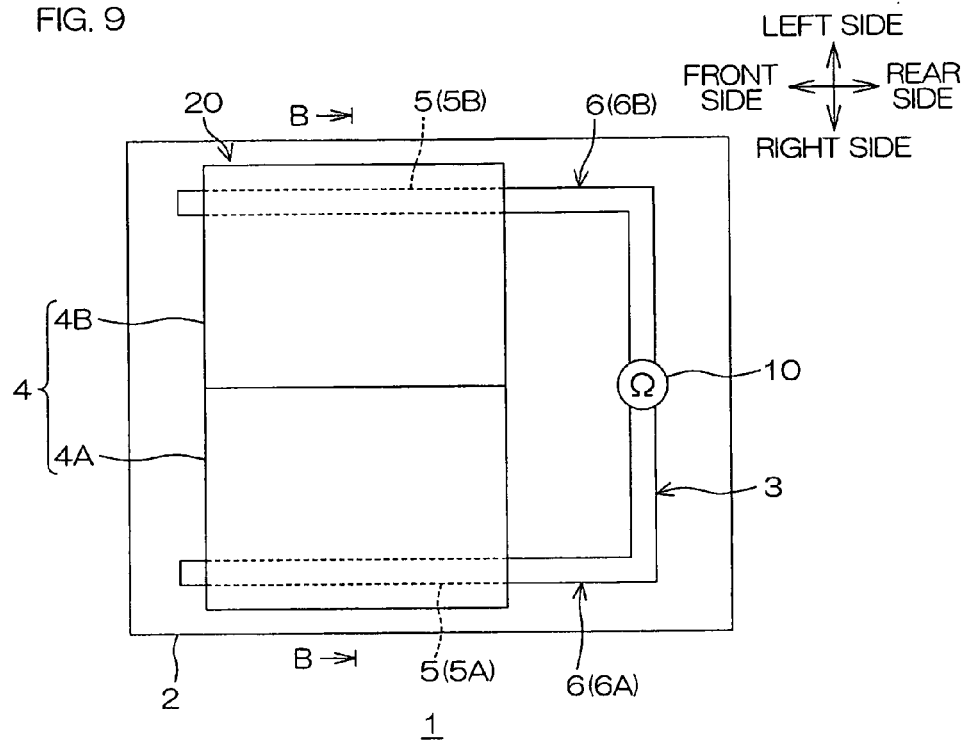
FIG. 9 is a plan view of another embodiment (an embodiment in which two conductive layers are in contact with each other) of the gas detection sensor according to the present invention.
Figure 10:
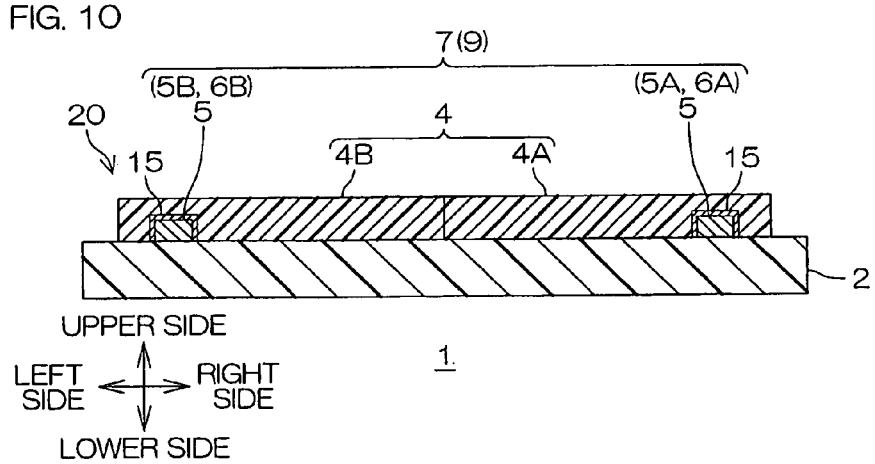
FIG. 10 is a sectional view taken along the line B-B of FIG. 9.

In FIGS. 9 and 10, the first conductive layer 4A and the second conductive layer 4B are in contact with each other on the left end face of the first conductive layer 4A and the right end face of the second conductive layer 4B. Thus, the first conductive layer 4A and the second conductive layer 4B are electrically connected with each other.

In the gas detection sensor 1, there is no need to provide the bridge wire 9, so that the configuration can be simplified. Besides, the absence of the bridge wire 9 eliminates the need to consider the resistance in the bridge wire 9, which can ensure gas detection with even higher accuracy.

Figure 11:
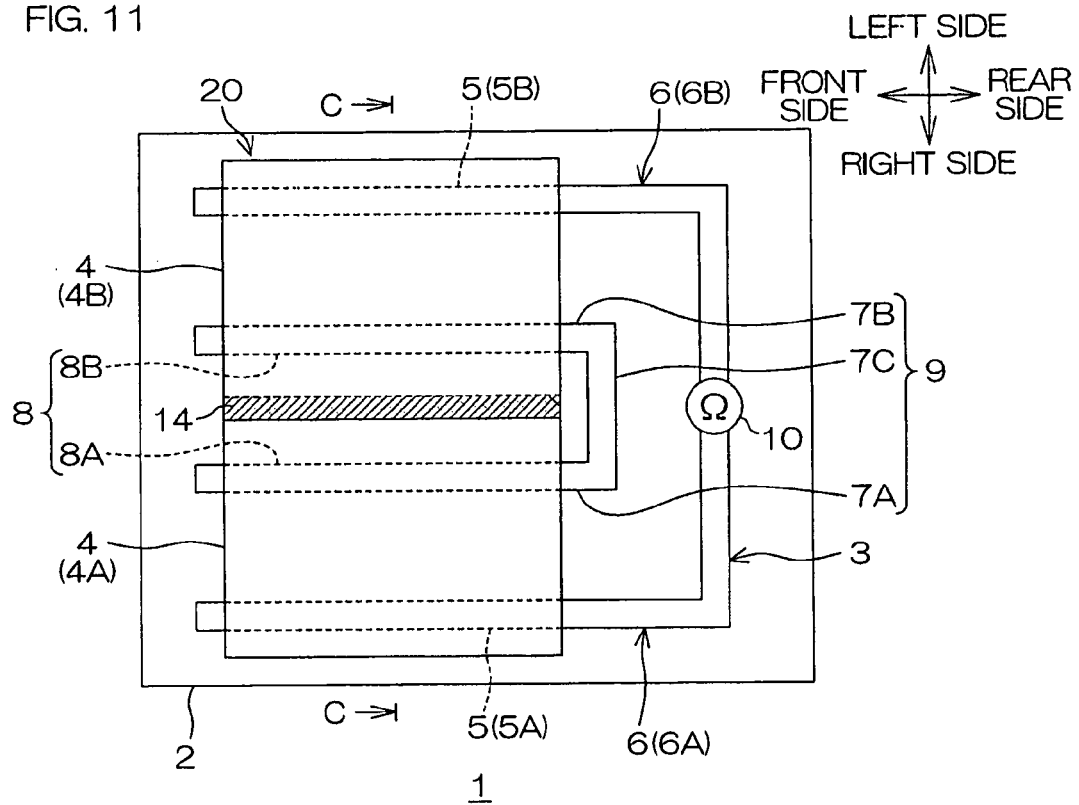
FIG. 11 is a plan view of another embodiment (an embodiment in which conductive layers have an overlapping portion) of the gas detection sensor according to the present invention.
Figure 12:
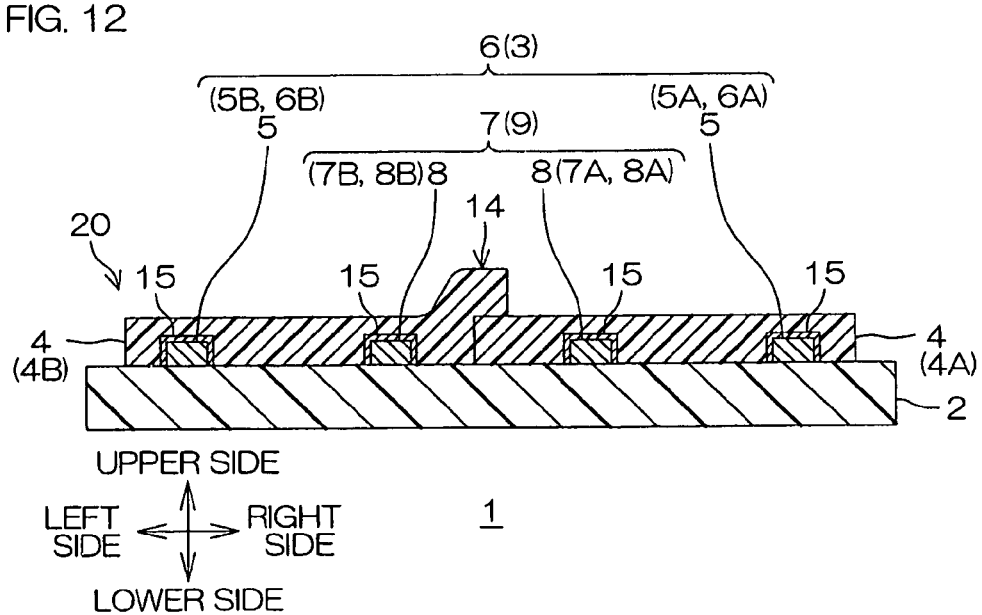
FIG. 12 is a sectional view taken along the line C-C of FIG. 11.

In the formation of the first and the second conductive layers 4A and 4B of FIGS. 9 and 10, when these two layers are sequentially formed by dividing, the right side end edge of the second conductive layer 4B may overlap on the left side end edge of the first conductive layer 4A as shown in FIGS. 11 and 12. In such case, the bridge wire 9 is preliminarily formed and thereafter, the first conductive layer 4A and the second conductive layer 4B are sequentially formed.

In the conductive layer 4, a portion (overlapping portion) 14 overlapping the left side end edge of the first conductive layer 4A and the right side end edge of the second conductive layer 4B is usually formed so as to extend in the front-and-rear direction.

The bridge wire 9 is connected to the first conductive layer 4A and the second conductive layer 4B which are adjacent in the left-and-right direction so that the first connecting wire 7A and the second connecting wire 7B sandwich the overlapping portion 14 in the left-and-right direction.

In the gas detection sensor 1, when the overlapping portion 14 is formed in the conductive layer 4, the thickness of the conductive layer 4 in the overlapping portion 14 becomes thicker than that of its surrounding. This makes the swelling ratio of the non-conductive substance in the overlapping portion 14, caused by absorption or adsorption of gas during gas detection, higher than that of the non-conductive substance around the overlapping portion 14. Therefore, the change in the electrical resistance value in the overlapping portion 14 becomes larger than the change in the electrical resistance value around the overlapping portion 14. Further, when the bridge wire 9 is not provided, an electrical pathway (path) between the first electrode 5A and the second electrode 5B is formed so as to pass through the overlapping portion 14.

Therefore, a significant change in the electrical resistance value caused by the overlapping portion 14 is detected by the electrical resistance detector 10, which may deteriorate the accuracy of the gas detection.

However, in the gas detection sensor 1 of FIGS. 11 and 12, even if the overlapping portion 14 is formed in the conductive layer 4, the bridge wire 9 is provided. Therefore, the path between the first electrode 5A and the second electrode 5B is formed so as to bypass the overlapping portion 14 and pass through the third connecting wire 7C. At the same time, the first conductive layer 4A and the second conductive layer 4B are reliably connected by the first connecting wire 7A and the second connecting wire 7B of the bridge wire 9, respectively, through the third connecting wire 7C. As a result, gas detection can be ensured with high accuracy.

Example

While in the following, the present invention is described in further detail with reference to Examples and Comparative Example, the present invention is not limited to any of them.
(Production of Gas Detection Sensor)

Example 1

A liquid crystal polymer copper-clad laminate (product number: ESPANEX L-12-25-00NE, single-sided, standard type, manufactured by Nippon Steel Chemical Co., Ltd.) in which a 12 μm-thick copper foil as a conductive layer was preliminarily laminated on the upper surface of a 25 μm-thick liquid crystal polymer sheet as an insulating layer was prepared, and an electrode pattern and a bridge wire having the above-mentioned pattern were simultaneously formed by a subtractive method (see FIGS. 1 and 3(b)).

Each of the first and the second electrode wires had a length of 20 mm and a width of 0.25 mm, and a spacing (D1) between the first and the second electrode wires was 5 mm. The bridge wire had a width of 0.25 mm, each of the first and the second connecting wires had a length of 19 mm, and a spacing (D2) therebetween was 2.5 mm. Each of a spacing between the first electrode wire and the first connecting wire and a spacing between the second electrode wire and the second connecting wire was 1.3 mm, and a spacing (D3) between the rear end portion of the electrode wire and the third connecting wire was 1 mm.

Then, a 0.5 μm-thick gold layer serving as a protective layer was formed on surfaces of the electrode pattern and the bridge wire (see FIG. 3(c)).

Subsequently, 40 mg of carbon black (Black pearl 2000), 150 mg of polyvinyl alcohol, and 20 mL of THF were blended and mixed to prepare a conductive component-containing liquid.

The conductive component-containing liquid thus obtained was then sprayed onto the insulating layer using an ultrasonic spray nozzle (AccuMist Nozzle, manufactured by Sono-Tek Corporation) through a mask having an opening (opening area of 30 mm$^2$) formed in a rectangular shape in plane view of a 1.67 mm width (length in the left-and-right direction) and a 18 mm length (length in the front-and-rear-direction) (see FIG. 3(d)).

More particularly, the conductive component-containing liquid was sprayed in twice. Specifically, first, the insulating layer was covered with the above-mentioned mask so that the opening was opposed to the right side of the insulating layer, and the conductive component-containing liquid was then sprayed in a pattern corresponding to the first conductive layer. Subsequently, the mask was moved to the left side, the insulating layer was covered with the mask so that the opening was opposed to the left side of the insulating layer, and the conductive component-containing liquid was sprayed in a pattern corresponding to the second conductive layer. By doing this, the first conductive layer and the second conductive layer were sequentially formed by dividing.

To spray the conductive component-containing liquid, the frequency of the ultrasonic wave was set to 60 kHz, and an assist gas (air gas, a discharge pressure of 0.4 kPa, and a nozzle diameter of approximately 1 mm) was introduced at 25° C. The distance from the distal end of the ultrasonic spray nozzle to the insulating layer was 4 cm.

Example 2

The gas detection sensor was produced in the same manner as in Example 1 except that two bridge wires were formed in place of one bridge wire, and that three conductive layers (a first conductive layer, a second conductive layer, and a third conductive layer) were formed in place of two conductive layers (the first and the second conductive layers) (see FIG. 4).

Incidentally, the spacing (D2) between the first connecting wire and the second connecting wire in each of the bridge wires was 1.65 mm, and each of the spacing between the first electrode wire and the first connecting wire of the first bridge wire, the spacing between the second electrode wire and the second connecting wire of the second bridge wire, and the spacing between the second connecting wire of the first bridge wire and the first connecting wire of the second bridge wire was 1.3 mm.

Further, the conductive component-containing liquid was sprayed three times. A mask having an opening (opening area of 20 mm$^2$) formed in a rectangular shape in plane view of a 1.11 mm width (length in the left-and-right direction) and an 18 mm length (length in the front-and-rear-direction) was used during the spraying.

Example 3

The gas detection sensor was produced in the same manner as in Example 2 except that the shape of the bridge wire was changed from a generally U-shape in plane view to the shape of a thin flat sheet (see FIG. 5).

Incidentally, the bridge wire was formed so that its outer shape was the same as the outer peripheral edge of the bridge wire in Example 2.

Comparative Example 1

Figure 13:
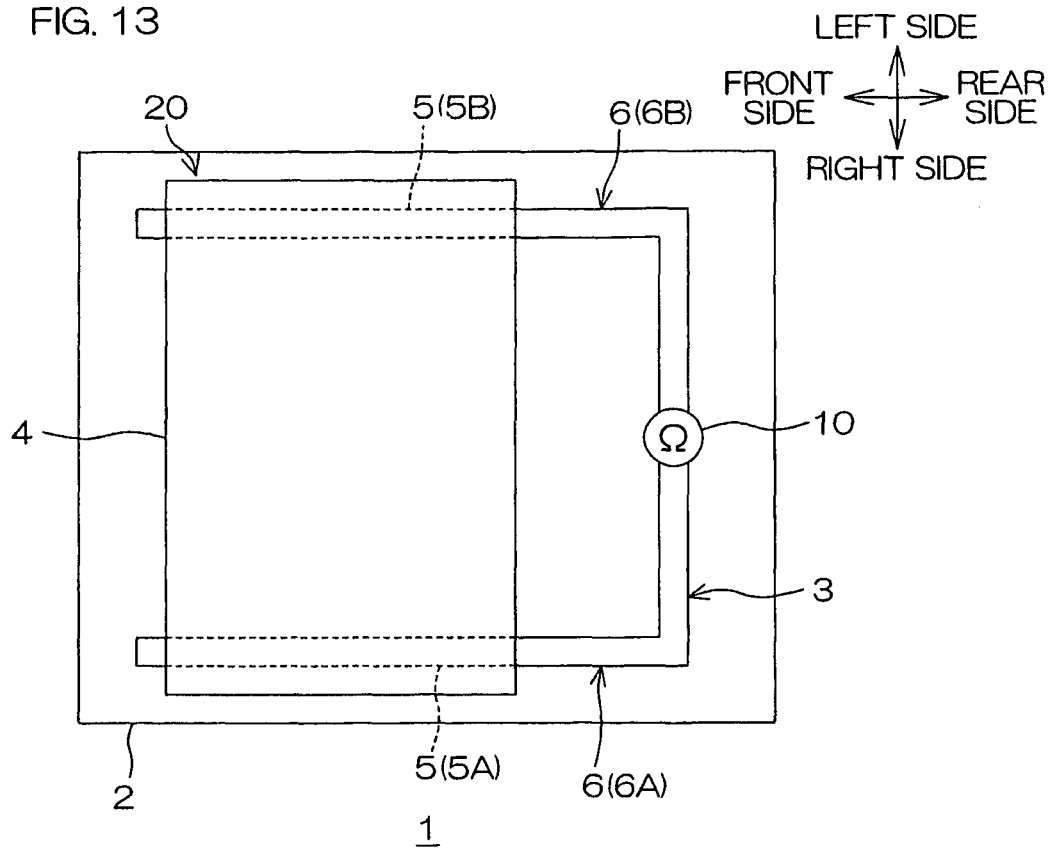
FIG. 13 is a plan view of the gas detection sensor (an embodiment in which one conductive layer is continuously formed) of Comparative Example 1.

The gas detection sensor was produced in the same manner as in Example 1 except that the electrode pattern was not provided and that one conductive layer was continuously formed in place of two conductive layers (the first and the second conductive layers) (see FIG. 13).

Incidentally, in the spraying of the conductive component-containing liquid, a mask having an opening (opening area of 60 mm$^2$) formed in a rectangular shape in plane view of a 3.33 mm width (length in the left-and-right direction) and a 18 mm length (length in the front-and-rear-direction) was used to form conductive layers at once.

(Evaluation)
(Resistance Between Electrodes)

A resistance value between the first electrode and the second electrode in the gas detection sensor produced according to each of Examples and Comparative Example was repeatedly measured 10 times with an ohm tester. The results are shown in Table 1.

(Sensor Function)

The gas detection sensor produced in each of Examples and Comparative Example was exposed to a gas (steam) atmosphere containing ethanol gas at a known concentration and the ethanol gas in the atmosphere was detected.

As a result, the ethanol gas at the known concentration was able to be detected by the gas detection sensors of Examples 1 to 3 and Comparative Example 1. After the gas detection was repeated 5 times to measure the ethanol gas, the results showed that the gas detection sensors of Examples 1 to 3 had a lower dispersion (standard deviation) than the gas detection sensor of Comparative Example 1.

TABLE 1

| Ex./Comp. Ex. | | Ex. 1 | Ex. 2 | Ex. 3 | Comp. Ex. 1 |
|---|---|---|---|---|---|
| Area of Each Conductive Layer (mm$^2$) | | 30 | 20 | 20 | 60 |
| Area of Entire Conductive Layer (mm$^2$) | | 60 | 60 | 60 | 60 |
| Resistance Value Between First Electrode and Second Electrode | Standard Deviation | 3 | 1.3 | 1.3 | 5 |
| | Average Value (kΩ) | 21.8 | 21.2 | 21.2 | 19.3 |
| | Maximum Value (kΩ) | 27 | 23 | 23 | 30 |
| | Minimum Value (kΩ) | 13 | 19 | 19 | 10 |

While the illustrative embodiments of the present invention are provided in the above description, such is for illustrative purpose only and it is not to be construed limitative. Modification and variation of the present invention which will be obvious to those skilled in the art is to be covered by the following claims.

What is claimed is:

1. A substance detection sensor comprising:
an insulating layer;
two electrodes spaced in opposed relation to each other on the insulating layer; and
conductive layers formed between the two electrodes on the insulating layer, and of which a swelling ratio varies depending on at least one of the type or amount of a specific gas, the conductive layers being formed by dividing a layer into plural layers between the two electrodes, so as to be disposed adjacently with a space provided therebetween in a direction in which the two electrodes oppose each other,
wherein a wire which is connected to the conductive layers is further provided, and the wire is provided on the inner sides of the pair of the electrodes in the opposed direction in spaced relation thereto and integrally includes:
a first connecting wire disposed on a first side in the direction in which the two electrodes oppose each other in the substance detection sensor, and connected to one of the conductive layers,
a second connecting wire disposed on a second side in the direction in which the two electrodes oppose each other in the substance detection sensor and spaced apart from the first connecting wire, and connected to the conductive layer disposed adjacently on the second side in the direction in which the two electrodes oppose each other in the substance detection sensor, and
a third connecting wire that connects the first connecting wire and the second connecting wire, wherein the wire is not in direct physical contact with the electrodes.

* * * * *